(12) United States Patent
Murray et al.

(10) Patent No.: US 11,395,661 B2
(45) Date of Patent: Jul. 26, 2022

(54) SPRING LOADED MECHANISM FOR THE DEPLOYMENT OF A HEMOSTATIC CLIP

(71) Applicant: BOSTON SCIENTIFIC SCIMED, INC., Maple Grove, MN (US)

(72) Inventors: Collin Murray, Maynard, MA (US); Henry Stock, Sanbornton, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 275 days.

(21) Appl. No.: 16/909,787

(22) Filed: Jun. 23, 2020

(65) Prior Publication Data

US 2021/0022745 A1    Jan. 28, 2021

Related U.S. Application Data

(60) Provisional application No. 62/876,864, filed on Jul. 22, 2019.

(51) Int. Cl.
| | | |
|---|---|---|
| *A61B 17/128* | (2006.01) | |
| *A61B 17/122* | (2006.01) | |
| *A61B 17/12* | (2006.01) | |

(52) U.S. Cl.
CPC ...... *A61B 17/1285* (2013.01); *A61B 17/1227* (2013.01); *A61B 2017/12004* (2013.01)

(58) Field of Classification Search
CPC . A61B 17/122; A61B 17/1227; A61B 17/128; A61B 17/1285; A61B 2017/12004
See application file for complete search history.

(56) References Cited

U.S. PATENT DOCUMENTS

| | | | |
|---|---|---|---|
| 5,527,320 A | 6/1996 | Carruthers et al. | |
| 8,062,311 B2 * | 11/2011 | Litscher | A61B 17/1285 606/143 |
| 8,080,021 B2 * | 12/2011 | Griego | A61B 17/1285 606/143 |

(Continued)

OTHER PUBLICATIONS

Anonymous: "Bayonet mount—Wikipedia", Wikipedia, XP055684465, Retrieved from the Internet: URL: https://en.wikipedia.org/w/index.php?title=Bayonet_mount&oldid=899225808 [retrieved on Apr. 8, 2020] $1^{st}$, $2^{nd}$ and $3^{rd}$ figure on p. 1. Paragraph [0001], May 29, 2019, 5 sheets.

*Primary Examiner* — Ryan J. Severson
(74) *Attorney, Agent, or Firm* — Fay Kaplun & Marcin, LLP

(57) ABSTRACT

A clipping system for treating tissue a clip with clip arms and an applicator having a flexible member and a control member. Proximal ends of the arms are received within a channel of a capsule. The capsule includes a slot extending from a proximal end of the capsule through a wall thereof. The control member includes a distal end connectable to the arms to move them between the open and closed configurations. A distal end of the flexible member includes a bushing having a distal portion receivable within a proximal end of the capsule. The distal portion includes an engaging tab extending laterally outward therefrom receivable within an engaging portion of the slot, a spring extending along the distal portion and disposed proximally of the engaging tab so that, when the engaging tab is received within the engaging portion, the spring is compressed against a portion of the capsule.

20 Claims, 3 Drawing Sheets

(56) References Cited

U.S. PATENT DOCUMENTS

| | | | |
|---|---|---|---|
| 10,905,434 B2* | 2/2021 | Estevez | A61B 17/1285 |
| 10,952,742 B2* | 3/2021 | Lehtinen | A61B 90/03 |
| 10,973,506 B2* | 4/2021 | Smith | A61B 17/00234 |
| 11,020,125 B2* | 6/2021 | Randhawa | A61B 17/1285 |
| 11,202,637 B2* | 12/2021 | Murray | A61B 17/1285 |
| 2005/0107809 A1* | 5/2005 | Litscher | A61B 17/1285 |
| | | | 606/142 |
| 2007/0112359 A1* | 5/2007 | Kimura | A61B 17/1222 |
| | | | 606/142 |
| 2013/0072946 A1* | 3/2013 | Terada | A61B 17/122 |
| | | | 606/157 |
| 2014/0088616 A1* | 3/2014 | Clerc | A61B 17/1285 |
| | | | 606/142 |
| 2018/0035997 A1 | 2/2018 | Smith et al. | |
| 2018/0049745 A1 | 2/2018 | Randhawa et al. | |
| 2018/0153552 A1* | 6/2018 | King | A61B 17/1285 |
| 2019/0090882 A1 | 3/2019 | Estevez et al. | |
| 2019/0159783 A1* | 5/2019 | Lehtinen | A61B 17/122 |
| 2020/0155159 A1* | 5/2020 | Murray | A61B 17/1285 |
| 2021/0015487 A1* | 1/2021 | Murray | A61B 17/1227 |
| 2021/0015488 A1* | 1/2021 | King | A61B 17/122 |
| 2021/0022745 A1* | 1/2021 | Murray | A61B 17/1285 |
| 2022/0071637 A1* | 3/2022 | Murray | A61B 17/122 |

* cited by examiner

SPRING LOADED MECHANISM FOR THE DEPLOYMENT OF A HEMOSTATIC CLIP

PRIORITY CLAIM

The present disclosure claims priority to U.S. Provisional Patent Application Ser. No. 62/876,864 filed Jul. 22, 2019; the disclosure of which is incorporated herewith by reference.

FIELD

The present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract, or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be used.

SUMMARY

The present disclosure relates to a clipping system for treating tissue, comprising a clip including a pair of clip arms. Each of the clip arms extends from a proximal end to a distal end, proximal ends of the clip arms slidably received within a channel of a capsule to be moved between an open configuration and a closed configuration. The capsule includes a slot extending from a proximal end of the capsule through a wall thereof. An applicator includes an elongated flexible member and a control member extending therethrough. The control member includes a distal end configured to be connected to the clip arms to move the clip arms between the open configuration and the closed configuration. A distal end of the elongated flexible member includes a bushing, the bushing including a distal portion receivable within the proximal end of the capsule. The distal portion includes an engaging tab extending laterally outward therefrom receivable within an engaging portion of the slot in a coupled configuration. A spring extends along the distal portion of the bushing and disposed proximally of the engaging tab so that, when the engaging tab is received within the engaging portion, the spring is compressed against a portion of the capsule. When the spring is compressed, it may provide a force which maintains the engaging tab within the engaging portion.

In an embodiment, the slot may include a first portion extending along an axis substantially parallel to a longitudinal axis of the capsule and a second portion extending along an axis angled with respect to the axis of the first portion, the first portion extending from an open first end to a second end, the second portion extending from the second end of the first portion to a third end extending toward the proximal end of the capsule, the third end defining the engaging portion of the slot.

In an embodiment, the second portion of the slot may be angled at an angle of between 20 and 60 degrees relative to the first portion of the slot so that, when the spring is further compressed during a deployment of the clip, the engaging tab slides from the third end toward the second end.

In an embodiment, the force produced by the spring to maintain the engaging tab within the engaging portion may be greater than a pre-determined force required to move the clip between the open and closed configurations so that the engaging tab remains seated within the engaging portion during a clipping of target tissue.

In an embodiment, the spring may be a coil spring extending helically about the distal portion of the bushing between the engaging tab and a distal end of a proximal portion of the bushing.

In an embodiment, the distal portion of the bushing may have a smaller diameter than the proximal portion thereof.

In an embodiment, the spring may be one of a leaf spring and a wave spring.

In an embodiment, the distal portion may taper toward a distal end thereof.

In an embodiment, the control member may be releasably connected to the clip arms via a yoke.

The present disclosure also relates to a clip device, comprising a clip including a capsule within which clip arms may be moved between an open configuration and a closed configuration. The capsule including a slot extending from a proximal end of the capsule through a wall thereof. A bushing is configured to releasably couple the clip to a proximal portion of the device. The bushing includes a distal portion receivable within the proximal end of the capsule. The distal portion includes an engaging tab extending laterally outward therefrom receivable within an engaging portion of the slot in a coupled configuration. A spring extends along the distal portion of the bushing and disposed proximally of the engaging tab so that, when the engaging tab is received within the engaging portion, the spring is compressed against a portion of the capsule. When the spring is compressed, it may provide a force which maintains the engaging tab within the engaging portion.

In an embodiment, the slot may include a first portion extending along an axis substantially parallel to a longitudinal axis of the capsule and a second portion extending along an axis angled with respect to the axis of the first portion, the first portion extending from an open first end to a second end, the second portion extending from the second end of the first portion to a third end extending toward the proximal end of the capsule, the third end defining the engaging portion of the slot.

In an embodiment, the second portion of the slot may be angled at an angle of between 20 and 60 degrees relative to the first portion of the slot so that, when the spring is further compressed during a deployment of the clip, the engaging tab slides from the third end toward the second end.

In an embodiment, the force produced by the spring to maintain the engaging tab within the engaging portion may be greater than a pre-determined force required to move the clip between the open and closed configurations so that the engaging tab remains seated within the engaging portion during a clipping of target tissue.

In an embodiment, the spring may be a coil spring extending helically about the distal portion of the bushing between the engaging tab and a distal end of a proximal portion of the bushing.

In an embodiment, the distal portion of the bushing may have a smaller diameter than the proximal portion thereof.

The present disclosure also relates to a method for clipping a target tissue. A clip is coupled with a bushing of an applicator by inserting a distal portion of the bushing through a proximal end of a capsule of the clip so that an engaging tab of the bushing, which extends laterally outward from the distal portion of the bushing is received within a slot extending from the proximal end of the capsule through a wall thereof. The bushing is rotated about a longitudinal axis thereof so that the engaging tab is received within an engaging portion of the slot, a spring extending along the distal portion of the bushing proximally of the engaging tab being compressed against a portion of the capsule to provide a force which maintains the engaging tab within the engaging portion, in a coupled configuration.

DETAILED DESCRIPTION

Figure 1:
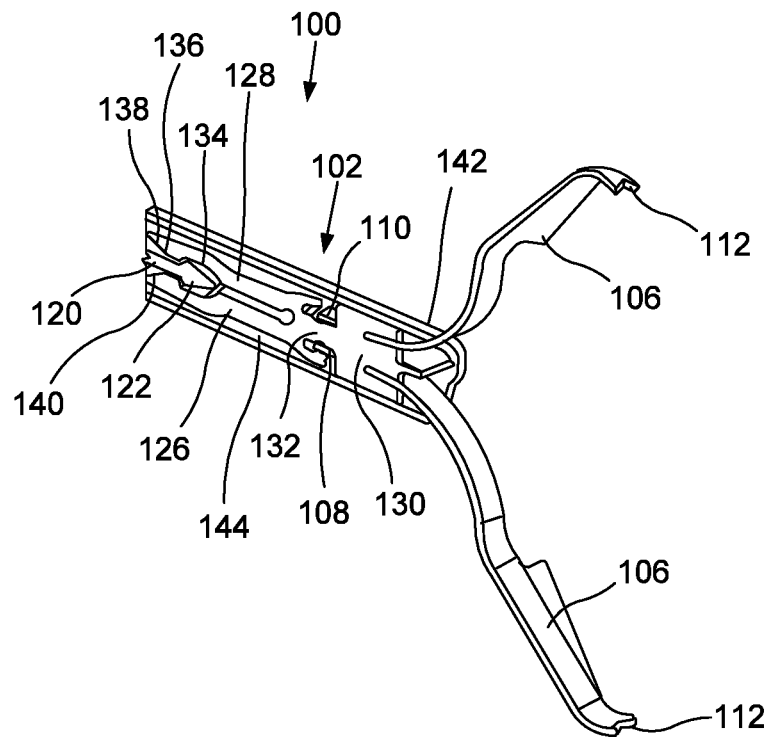
FIG. 1 shows a cross-sectional perspective view of a distal portion of a clipping system according to an exemplary embodiment of the present disclosure.

The present disclosure may be further understood with reference to the following description and the appended drawings, wherein like elements are referred to with the same reference numerals. The present disclosure relates to a clipping system and, in particular, relates to endoscopic clipping system, in which a clip may be loaded onto a distal end of an applicator prior to an endoscopic procedure. Exemplary embodiments of the present disclosure comprise a clip including clip arms slidable within a capsule to move between an open configuration and a closed configuration to clip tissue, as desired, and an applicator coupleable thereto via a spring loaded mechanism. The spring loaded connection between the clip and the applicator facilitates a direct releasable connection with the applicator, which also facilitates deployment of the clip from the applicator. It will be understood by those of skill in the art that the terms proximal and distal as used herein, are intended to refer to a direction toward and away from, respectively, a user of the device.

As shown in FIGS. 1-6, a clipping system 100 comprises a clip 102 configured to be loaded onto an applicator 104 prior to insertion of the system 100 into a body to clip target tissue therein. The clip 102 includes a pair of clip arms 106, proximal ends 110 of which are slidably received within a capsule 108 so that the clip arms 106 may move between an open configuration, in which distal ends 112 of the clip arms 106 are separated from one another, and a closed configuration, in which distal ends 112 are drawn toward one another to grip tissue. A proximal end 114 of the capsule 108 may be coupled to a bushing 116 of the applicator 104 via a spring loaded mechanism 118 which, as will be described in further detail below, maintains a coupling between the capsule 108 and the applicator 104 upon a loading of the clip 102 onto the applicator 104 and facilitates a separation of the capsule 108 from the bushing 116 during a deployment of the clip 102.

In one embodiment, the clipping system 100 may be reloadable so that after deployment of the clip 102, a new clip 102 may be loaded onto the applicator 104 so that the same applicator 104 may be used to deliver the new clip 102 to a second portion of target tissue in the body. It will be understood by those of skill in the art, however, that the applicator 104 is not required to be reloadable and that the spring loaded mechanism 118 for connecting the capsule 108 and the bushing 116 may also be utilized for single use clipping systems.

As shown in FIGS. 1, the clip 102 includes the pair of clip arms 106, proximal ends 110 of which are, in this embodiment, connected to one another via a yoke 126 slidably received within the capsule 108. In this embodiment, the clip arms 106 are biased toward the open configuration so that, when not constrained by the capsule 108, the clip arms 106 move under their natural bias to the open configuration in which the distal ends 112 of the clip arms 106 spread apart from one another to receive tissue therebetween. When the clip arms 106 are drawn into the capsule 108, the capsule 108 constrains the clip arms 106, holding the distal ends 112 together so that tissue may be gripped therebetween. The yoke 126 is longitudinally slidable within the capsule 108 to move the clip arms 106 proximally and distally relative to the capsule 108 between the open and closed configurations.

Each of the clip arms 106 extends from the proximal end 110, connected to the yoke 126, to the distal end 112. The distal ends 112 of one or both of the clip arms 106 may include tips extending laterally inward toward the other clip arm 106 with the tips including, for example, teeth, protrusions, spikes or other structures configured to grip tissue between the distal ends 112. One or both of the clip arms 106 may also include a locking feature configured to lock the clip arms 106 in the tissue gripping configuration after target tissue has been gripped as desired by the clip arms 106. In one embodiment, one or both of the clip arms 106 includes a locking tab extending laterally outward therefrom configured to engage a portion of the capsule 108 when the clip arms 106 have been drawn into the capsule 108 by a predetermined distance. For example, the locking tabs may be received within correspondingly sized, shaped and positioned locking windows extending laterally into or through a wall of the capsule 108 to lock the clip arms 106 relative to the capsule 108, in the tissue gripping configuration.

The yoke 126 is connected to the proximal ends 110 of the clip arms 106 and is configured to be connected to an enlarged distal end 122 of a control member 120. In this embodiment, the yoke 126 includes a proximal portion 128 and a distal portion 130 connected to one another at a point located at reference numeral 132 configured to break or separate when subject to a force exceeding a predetermined threshold value. For example, the point 132 may include a welding, a decreased diameter portion, or an adhesive, or combinations thereof, that breaks or otherwise uncouples when sufficient force is exerted thereon. The distal portion 130 is configured to engage proximal portions of the clip arms 106 via, for example, a pair of protrusions extending therefrom and received within correspondingly sized and shaped openings extending through proximal portions of the clip arms 106 so that the clip arms 106 are held in position relative to one another.

The proximal portion 128 is configured to engage the enlarged distal end 122 of the control member 120. In one embodiment, the proximal portion 128 includes a cavity 134 sized and shaped to receive the enlarged distal end 122 and a longitudinal slot 136 extending proximally from the cavity 134 to a proximal end 138 of the yoke 126. The longitudinal slot 136 is sized and shaped to receive a portion of the control member 120 extending proximally from the enlarged distal end 122. In one embodiment, an opening of the longitudinal slot 136 at the proximal end 138 includes an angled surface 140 tapering toward a distal end thereof to facilitate insertion of the enlarged distal end 122 distally through the longitudinal slot 136 and into the cavity 134 during loading the clip 102 onto the applicator 104. The cavity 134 and the longitudinal slot 136 are configured so that, once the enlarged distal end 122 has been inserted, or forced, through the slot 136 into the cavity 134, the slot 136 retracts in diameter to prevent the enlarged distal end 122 from being proximally withdrawn therefrom. Thus, longitudinal movement of the control member 120 relative to the capsule 108 moves the clip arms 106 between the open and the closed configurations.

It will be understood by those of skill in the art that the yoke 126, as described above, is exemplary only, and may include other configurations depending on any number of considerations such as, for example, whether the clipping system 100 is intended to be reloadable or single use. For example, according to another embodiment, rather than including a slot 136 via which the distal end 122 of the control member 120 may be inserted into the proximal portion 128, the proximal portion 128 may be connected or otherwise attached to the control member 120 during a manufacturing of the clipping system 100. According to yet another embodiment, rather than having a single yoke 126 including two portions connected to one another at a breakable point 132, the yoke 126 may comprise two separate elements that are connected to one another via a releasable coupling such as, for example, corresponding mating features.

The capsule 108 extends longitudinally from the proximal end 114 to a distal end 142 and includes a channel 144 extending longitudinally therethrough. The channel 144 is sized and shaped to slidably receive the yoke 126 and the clip arms 106 therein. As described above, the capsule 108 of this embodiment also includes locking structures (e.g., locking windows) for engaging corresponding locking features (e.g., locking tabs) of the clip arms 106. The capsule 108 also includes a slot 146, as shown in FIGS. 3-6, extending through a wall of the capsule 108 along a proximal portion of the capsule 108 to receive an engaging tab 148 of the bushing 116.

The slot 146 extends along an angled path, including a first portion 150 and a second portion 156 extending at an angle relative to one another. In some embodiments, the first portion 150 extending along an axis substantially parallel to a longitudinal axis of the capsule 108 from an open first end 152 at the proximal end 114 of the capsule 108 to a second end 154. The second portion 156 extends along an axis that is angled with respect to the axis of the first portion 150 from the second end 154 of the first portion 150 to a third end 158, which extends toward the proximal end 114 of the capsule 108. The axis of the second portion 156 is angled relative to the angle of the first portion 150 at an angle of between, for example, 0 to 90 degrees.

In one embodiment, the axis of the second portion 156 is angled relative to the angle of the first portion 150 at an angle of between, for example, 10 to 90 degrees, or 20 to 60 degrees. The angle is limited by a size of the slot 146, and forces that are desired for deployment. As will be described in further detail below, upon loading of the clip 102 onto the applicator 104, the engaging tab 148 of the bushing 116 will be seated in and maintained within the third end 158 via a spring 160 of the bushing 116.

Figure 2:
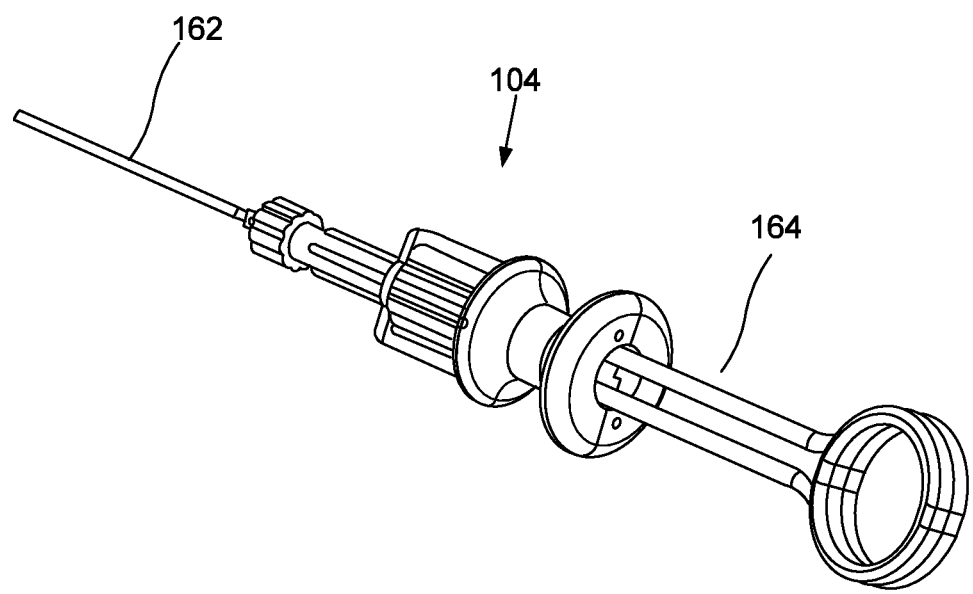
FIG. 2 shows a perspective view of an applicator according to the system of FIG. 1.

As shown in FIG. 2, the applicator 104 includes a flexible member 162 such as, for example, a catheter extending from a proximal end connected to a handle portion 164 that remains outside of the body during the clipping of target tissue, to a distal end including, for example, the bushing 116 for connecting the applicator 104 to the clip 102. The control member 120 extends through the flexible member 162 from a proximal end connected to the handle portion 164, which includes actuators for controlling a movement of the clip 102 once the clip 102 has been loaded onto the applicator 104, to the enlarged distal end 122.

In this embodiment, the bushing 116 is connected to the distal end of the flexible member 162 and is configured to be connected to the clip 102 via the spring loaded mechanism 118, which includes the engaging tab 148 and the spring 160, as shown in FIGS. 3-6. In one embodiment, the bushing 116 extends longitudinally and includes a distal portion 166 configured to engage the capsule 108 and a proximal portion 168, which is connected to a distal end of the flexible member 162. A channel extends through the bushing 116 so that, when the bushing 116 is coupled to the capsule 108, the channel of the bushing 116 is substantially aligned with the channel 144 of the capsule 108. The distal portion 166 may have a smaller cross-sectional area (e.g., diameter) than the proximal portion 168 and is sized and shaped to be received within the proximal end 114 of the capsule 108. The distal portion 166 includes the engaging tab 148, which extends laterally outward from a distal end 170 thereof.

The engaging tab 148 is configured to be received within the slot 146 when the distal end 170 of the distal portion 166 is inserted into the capsule 108. In one embodiment, the distal portion 166 tapers toward the distal end 170 to facilitate insertion of the distal portion 166 into the capsule 108. The spring 160 extends along the distal portion 166, proximally of the engaging tab 148. In one example, the spring 160 may be a coil (e.g. helical) spring which extends about the distal portion 166 between the engaging element 148 and a distal end 172 of the proximal portion 168. Although the exemplary embodiment shows and describes a coil spring, it will be understood by those of skill in the art that the spring loaded mechanism 118 may include any of a variety of biasing elements such as, for example, a leaf spring or a wave spring.

Figure 3:
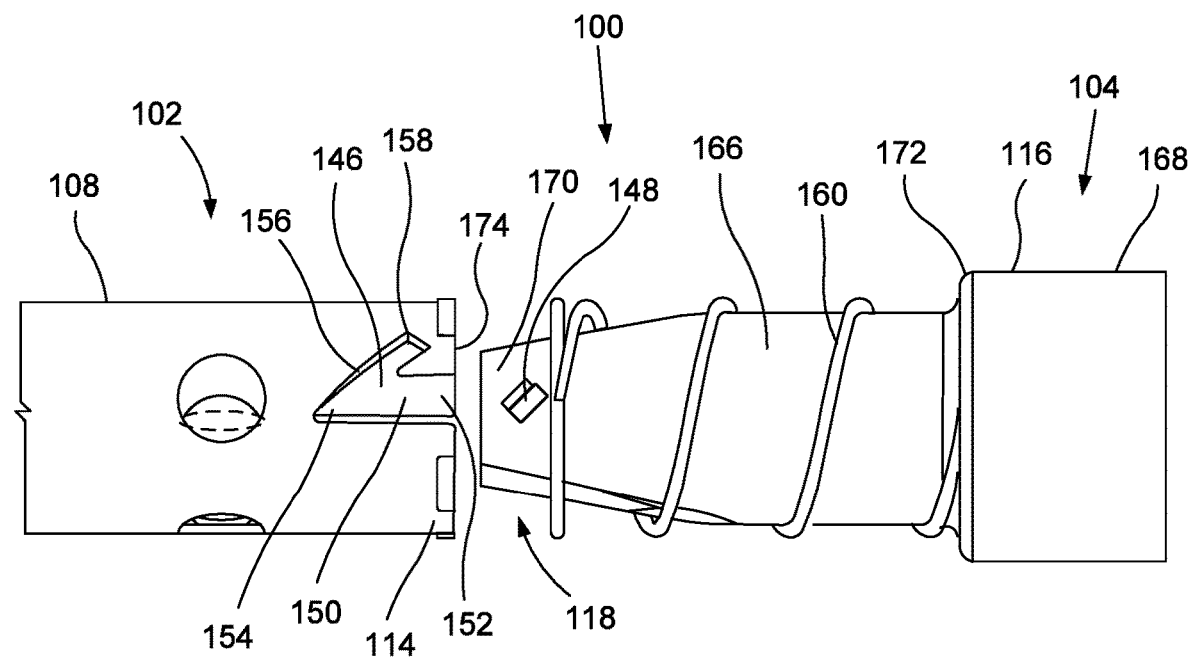
FIG. 3 shows an enlarged longitudinal side view of an exemplary spring loaded mechanism, prior to loading the clip onto the applicator, according to the system of FIG. 1.

During coupling of the clip 102 to the applicator 104, the bushing 116 is aligned with the capsule 108, as shown in FIG. 3, so that when the distal end 170 of the distal portion 166 is inserted into the proximal end 114 of the capsule 108, the engaging tab 148 is inserted through the open first end 152 of the slot 146 and moved distally therealong until the engaging tab 148 is received within the second end 154 thereof. As the engaging tab 148 is inserted distally through the slot 146, the spring 160 is compressed between a proximal face 174 of the capsule 108 and the distal end 172 of the proximal portion 168.

Figure 4:
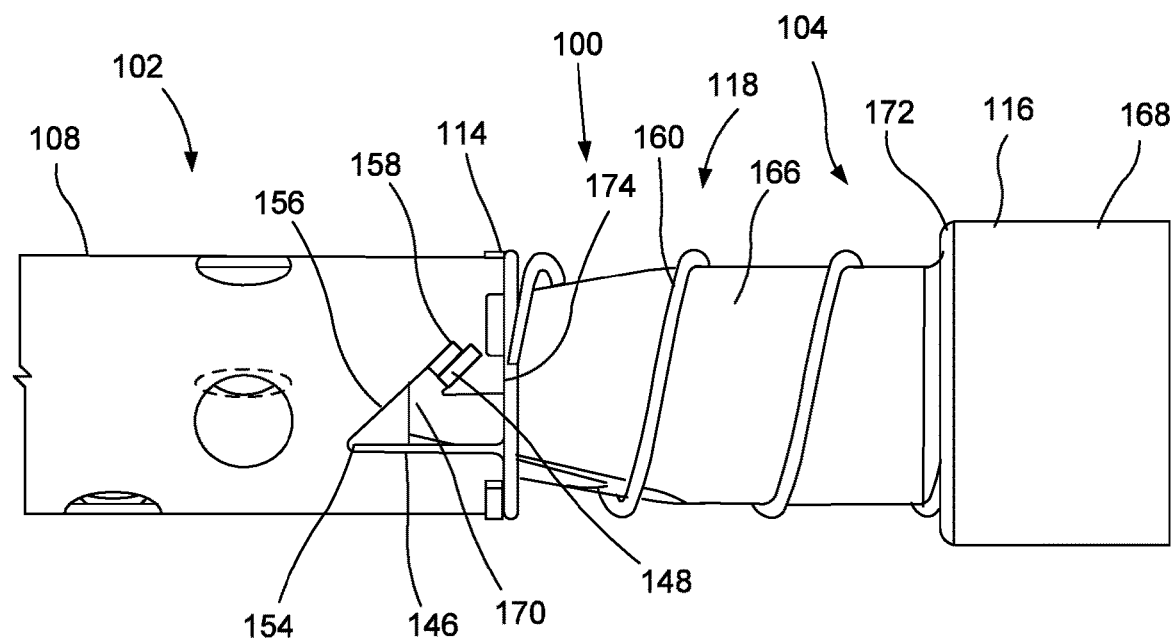
FIG. 4 shows an enlarged longitudinal side view of the spring loaded mechanism, during loading of the clip onto the applicator, according to the system of FIG. 1.

As will be understood by those of skill in the art, the spring 160 is biased toward an initial configuration so that, when compressed, the spring 160 exerts a distal force against the capsule 108. Once the engaging tab 148 is at the second end 154, the bushing 116 is rotated about a longitudinal axis thereof so that the engaging tab 148 slides along the second portion 156 of the slot 146 from the second end 154 to the third end 158, as shown in FIG. 4. The force created by the compression of the spring 160 holds the engaging tab 148 within the third end 158 of the slot 146. This force created by the spring 160 is greater than a pre-determined force required to move the clip 102 between the open and closed configurations, such that the engaging tab 148 remains seated within the third end 158 during clipping of the target tissue.

Although the bushing 116 is described as being moved distally into the capsule 108, it will be understood by those of skill in the art that, in an alternative embodiment, the capsule 108 may be drawn proximally over the distal end 170 of the distal portion 166 so that the engaging element 148 may be received within the slot 146. It will also be understood by those of skill in the art that although not shown, the control member 120 is moved distally past the distal end 170 of the bushing 116 to engage the yoke 126, as described above. Once the control member 120 has been connected to the clip arms 106 via the yoke 126 and the bushing 116 of has been coupled to the capsule 108, loading of the clip 102 onto the applicator 104 is complete.

In use, after the clip 102 has been loaded onto the applicator 104, the clip 102, in the closed configuration, is inserted into the body to a location adjacent to target tissue via, for example, a working channel of an endoscope. Once the clip 102 has reached the target tissue, the clip 102 is moved toward the open configuration to receive the target tissue between the distal ends 112 of the clip arms 106. The clip 102 may be moved between the open and the closed configurations until the target tissue has been clipped between the clip arms 106, as desired. Once the clip 102 is in the closed configuration clipping the target tissue as desired, the control member 120 (e.g., via actuators of the handle portion 164) is moved proximally with respect to the capsule 108 until locking features of the clip arms 106 engage corresponding locking structures of the capsule 108, locking the clip arms 106 relative to the capsule 108 in the closed configuration.

Figure 5:
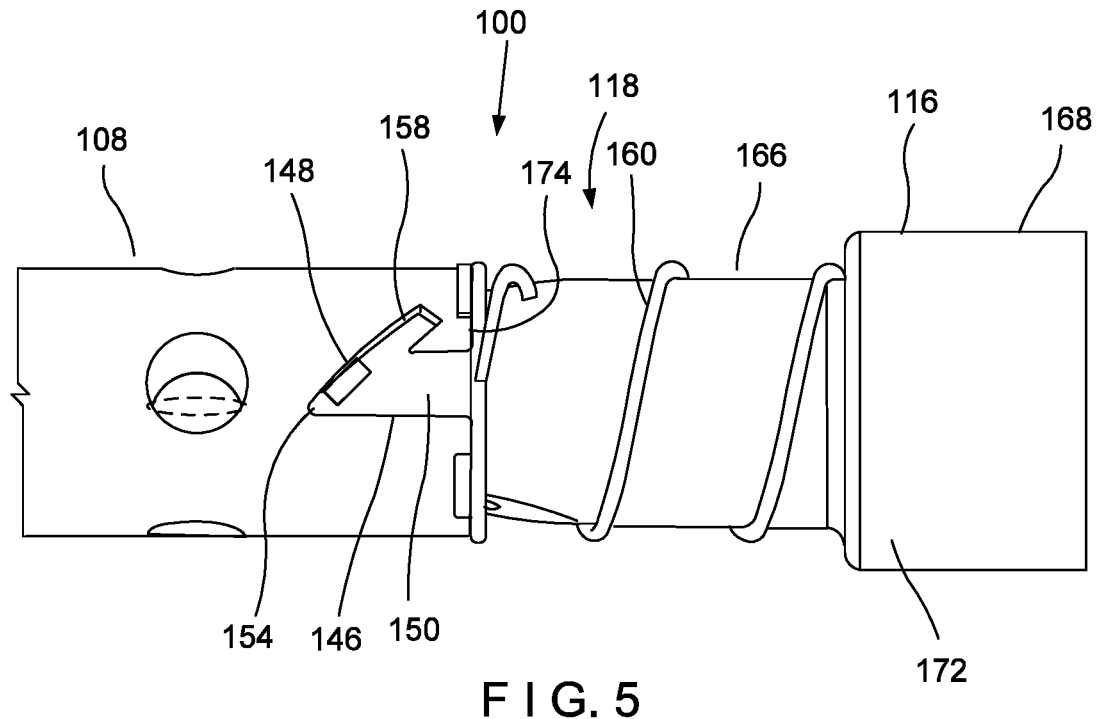
FIG. 5 shows an enlarged longitudinal side view of the spring loaded mechanism, during a deployment of the clip, according to the system of FIG. 1.

To deploy the clip 102 from the applicator, the control member 120 is drawn further proximally until the capsule 108 is drawn proximally relative to the bushing 118. Drawing the capsule 108 toward the bushing 116 results in a greater compression of the spring 160, which causes the engaging tab 148 to slide along the second portion 156 of the slot 146, from the third end 158 to the second end 154, as shown in FIG. 5. Once the engagement tab 148 has reached the second end 148, a force on the control member 120 is increased until the yoke 126 is broken and/or separated at the point 132, releasing the clip arms 106 from the control member 120.

Figure 6:
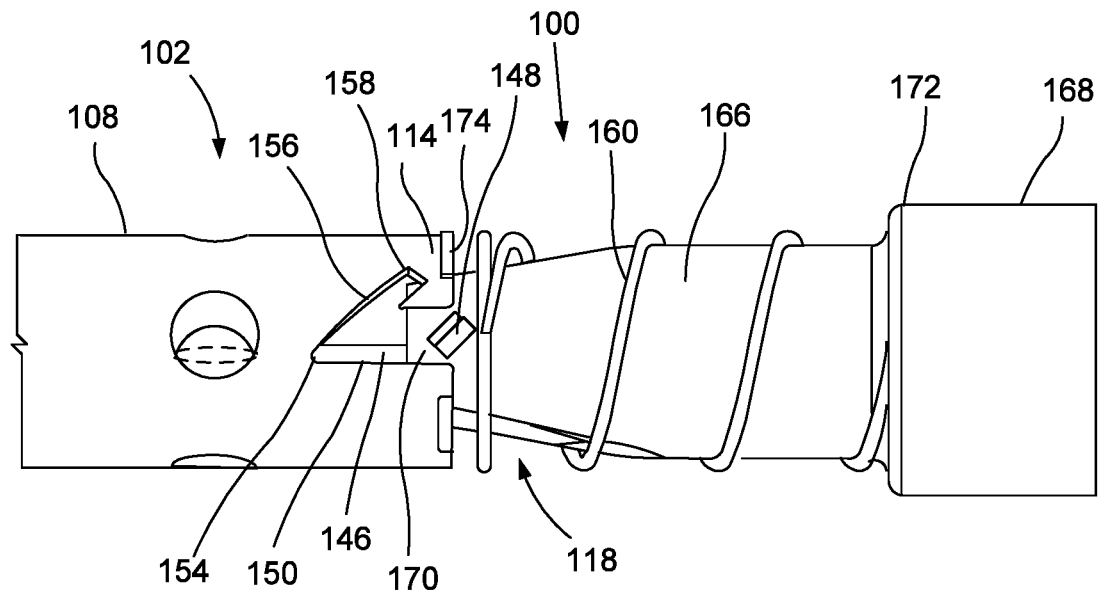
FIG. 6 shows an enlarged longitudinal side view of the spring loaded mechanism, upon deployment of the clip, according to the system of FIG. 1.

Upon release of the clip arms 106, the spring 160 reverts toward its biased configuration, pushing the capsule 108, and thereby the clip 102, distally relative to the bushing 116, as shown in FIG. 6. As the clip 102 is moved distally relative to the bushing 116, the engaging element 148 is moved proximally along the slot 146 until the engaging element 148 is completely removed from the slot 146 and the clip 102 is entirely detached from the applicator 104. The entire applicator 104, including the control member 120 and the proximal portion 128 of the yoke 126, may then be withdrawn proximally from the body leaving the clip 102 clipped over the target tissue.

As described above, where the clipping system 100 is a reloadable system, once the clip 102 has been deployed, a new clip 102 may be loaded onto the applicator 104, in the same manner as described above, so that the system 100 may then be used to clip a second portion of tissue. This process may be repeated using the same applicator 104 as many times as needed or desired. It will be understood by those of skill in the art, however, that the clipping system 100 is not required to be reloadable. It will also be understood that, while a process for separating the clip arms 106 from the control member 120 may vary depending on a type of clipping system (e.g., reloadable or single use) and a configuration of the yoke 126, the separation of the capsule 108 and the bushing 116 via the spring loaded mechanism 118, as described above, remains the same.

It will be apparent to those skilled in the art that various modifications may be made in the present disclosure, without departing from the scope of the disclosure.

What is claimed is:

1. A clipping system for treating tissue, comprising:
a clip including a pair of clip arms, each of the clip arms extending from a proximal end to a distal end, proximal ends of the clip arms slidably received within a channel of a capsule to be moved between an open configuration and a closed configuration, the capsule including a slot extending from a proximal end of the capsule through a wall thereof; and
an applicator including an elongated flexible member and a control member extending therethrough, the control member including a distal end configured to be connected to the clip arms to move the clip arms between the open configuration and the closed configuration, a distal end of the elongated flexible member including a bushing, the bushing including a distal portion receivable within the proximal end of the capsule, the distal portion including an engaging tab extending laterally outward therefrom receivable within an engaging portion of the slot in a coupled configuration, a spring extending along the distal portion of the bushing and disposed proximally of the engaging tab so that, when the engaging tab is received within the engaging portion, the spring is compressed against a portion of the capsule.

2. The system of claim 1, wherein the slot includes a first portion extending along an axis substantially parallel to a longitudinal axis of the capsule and a second portion extending along an axis angled with respect to the axis of the first portion, the first portion extending from an open first end to a second end, the second portion extending from the second end of the first portion to a third end extending toward the proximal end of the capsule, the third end defining the engaging portion of the slot.

3. The system of claim 2, wherein the second portion of the slot is angled at an angle of between 20 and 60 degrees relative to the first portion of the slot so that, when the spring is further compressed during a deployment of the clip, the engaging tab slides from the third end toward the second end.

4. The system of claim 1, wherein a force produced by the spring to maintaining the engaging tab within the engaging portion is greater than a pre-determined force required to move the clip between the open and closed configurations so that the engaging tab remains seated within the engaging portion during a clipping of target tissue.

5. The system of claim 4, wherein the distal portion of the bushing has a smaller diameter than the proximal portion thereof.

6. The system of claim 1, wherein the spring is a coil spring extending helically about the distal portion of the bushing between the engaging tab and a distal end of a proximal portion of the bushing.

7. The system of claim 1, wherein the spring is one of a leaf spring and a wave spring.

8. The system of claim 1, wherein the distal portion tapers toward a distal end thereof.

9. The system of claim 1, wherein the control member is releasably connected to the clip arms via a yoke.

10. A clip device, comprising:
a clip including a capsule within which clip arms may be moved between an open configuration and a closed configuration, the capsule including a slot extending from a proximal end of the capsule through a wall thereof; and
a bushing configured to releasably couple the clip to a proximal portion of the device, the bushing including a distal portion receivable within the proximal end of the capsule, the distal portion including an engaging tab extending laterally outward therefrom receivable within an engaging portion of the slot in a coupled configuration, a spring extending along the distal portion of the bushing and disposed proximally of the engaging tab so that, when the engaging tab is received within the engaging portion, the spring is compressed against a portion of the capsule.

11. The device of claim 10, wherein the slot includes a first portion extending along an axis substantially parallel to a longitudinal axis of the capsule and a second portion extending along an axis angled with respect to the axis of the first portion, the first portion extending from an open first end to a second end, the second portion extending from the second end of the first portion to a third end extending toward the proximal end of the capsule, the third end defining the engaging portion of the slot.

12. The device of claim 11, wherein the second portion of the slot is angled at an angle of between 20 and 60 degrees relative to the first portion of the slot so that, when the spring is further compressed during a deployment of the clip, the engaging tab slides from the third end toward the second end.

13. The device of claim 10, wherein a force produced by the spring to maintaining the engaging tab within the engaging portion is greater than a pre-determined force required to move the clip between the open and closed configurations so that the engaging tab remains seated within the engaging portion during a clipping of target tissue.

14. The device of claim 10, wherein the spring is a coil spring extending helically about the distal portion of the bushing between the engaging tab and a distal end of a proximal portion of the bushing.

15. The device of claim 14, wherein the distal portion of the bushing has a smaller diameter than the proximal portion thereof.

16. A method for clipping a target tissue, comprising:
coupling a clip with a bushing of an applicator by inserting a distal portion of the bushing through a proximal end of a capsule of the clip so that an engaging tab of the bushing, which extends laterally outward from the distal portion of the bushing is received within a slot extending from the proximal end of the capsule through a wall thereof; and
rotating the bushing about a longitudinal axis thereof so that the engaging tab is received within an engaging portion of the slot, a spring extending along the distal portion of the bushing proximally of the engaging tab being compressed against a portion of the capsule to provide a force which maintains the engaging tab within the engaging portion, in a coupled configuration.

17. The method of claim 16, wherein the slot includes a first portion extending along an axis substantially parallel to a longitudinal axis of the capsule and a second portion extending along an axis angled with respect to the axis of the first portion, the first portion extending from an open first end to a second end, the second portion extending from the second end of the first portion to a third end extending toward the proximal end of the capsule, the third end defining the engaging portion of the slot.

18. The method of claim 17, further comprising inserting the clip to a target area within a body via a working channel of an endoscope and moving the clip between an open configuration, in which distal ends of clip arms are separated from one another, and closed configurations, in which the distal ends of the clip arms are drawn toward one another, until a target tissue is clipped between the clip arms, wherein proximal ends of the clip arms are slidably received with a channel of the capsule to be moved between the open and closed configurations via a control member releasably coupled to the proximal ends of the clip arms.

19. The method of claim 18, further comprising deploying the clip over a target tissue by moving the capsule proximally relative to the bushing so that the spring is further compressed, a force produced by the compression of the spring during deployment causing the engaging tab to slide from the third end to the second end so that the applicator is removable from the capsule.

20. The method of claim 19, wherein deploying the clip over the target tissue includes drawing the control member proximally relative to the capsule until a proximal force exerted thereon exceeds a pre-determined force required to separate the control member from the clip arms.

* * * * *